US00PP11363P

United States Patent [19]

Kordes

[11] Patent Number: Plant 11,363

[45] Date of Patent: Apr. 25, 2000

[54] MINIATURE ROSE PLANT NAMED 'KORFRAUMA'

[75] Inventor: Wilhelm Kordes, Sparrieshoop, Germany

[73] Assignee: Bear Creek Gardens, Inc., Medford, Oreg.

[21] Appl. No.: 09/046,314

[22] Filed: Mar. 23, 1998

[51] Int. Cl.[7] ..... A01H 5/00

[52] U.S. Cl. ..... Plt./122

[58] Field of Search ..... Plt./122, 129

*Primary Examiner*—Howard J. Locker

*Attorney, Agent, or Firm*—Klarquist Sparkman Campbell Leigh & Whinston, LLP

[57] ABSTRACT

Miniature rose plant having a compact, vigorous, upright habit of growth; ability to root quickly from softwood cuttings; rapid flowering; good shelf life as a pot rose; resistance to powdery mildew; and excellent flower color stability.

1 Drawing Sheet

The present invention relates to a new and distinct variety of rose plant of the miniature class which was originated by me by crossing an unnamed, unpatented seedling (whose parents were 'KORexung'×'INTERmoto'), (unpatented), with an unnamed, unpatented seedling of unknown parentage.

The primary objective of this breeding was to produce a new miniature rose variety having a compact, vigorous, upright habit of growth; ability to root quickly from softwood cuttings; rapid flowering; good shelf life as a pot rose; resistance to powdery mildew; and excellent flower color stability. The objective was substantially achieved, along with other desirable improvements, as evidenced by the following unique combination of characteristics that are outstanding in the new variety and that distinguish it from its parents, as well as from all other varieties of which I am aware:

1. Compact growth habit;
2. Attractive cherry red blooms with good color stability;
3. Rapid rooting from softwood cuttings;
4. Long shelf life;
5. Resistance to powdery mildew.

'KORfrauma' is a miniature rose ideally suited to pot culture. Its rapid rooting, easy forcing to flower, and attractive, stable flower color are good attributes. Potted 'KORfrauma' rose plants also have a shelf life, i.e., a good showing of blooms, of at least 18 days after four days of transport.

Asexual reproduction of this new variety by cutting propagation, as performed at Sparrieshoop, Germany, and Wasco and Somis, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

In such illustration, the blooms shown along the top are blooms as viewed from above in the following stages starting with the leftmost bloom:

Bloom on day one starting to open;
Bloom on day two;
Bloom on day three;
Bloom on day four;
Bloom on day seven or eight.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (unpatented).

*Pollen parent.*—Unnamed seedling (unpatented).

Classification:

*Botanical.*—Rosa hybrida.

*Commercial.*—Miniature rose.

FLOWER

Observations made from specimens grown in a greenhouse environment at Sparrieshoop, Germany and at Somis, Calif. from January, 1997 to December, 1997.

Blooming habit: Continuous.

Bud:

*Size.*—Three-fourths inch when the petals start to unfurl.

*Form.*—The bud form is long, pointed ovoid.

*Color.*—When sepals first divide, bud color is Red Group 53B. When half blown, the upper sides of the petals are Red Group 43A and the lower sides of the petals are Red Group 53B.

*Sepals.*—Color: Green Group 138C. Surface texture: Covered in fine hairs. There are three normally appendaged sepals. There are two unappendaged sepals with hairy edges.

*Receptacle.*—Color: Green Group 137C. Shape: Funnel. Size: Small (7/32"×¼"). Surface: Smooth.

*Peduncle.*—Length: Short (1½"). Surface: Prickly and glandular. Color: Green Group 137B. Strength: Stiff, erect.

Bloom:

*Size.*—Small. Average open size is 1½ inches.

*Borne.*—Singly and several together in clusters having pyramidal shape of three to five flowers.

*Stems.*—Short. Average length is about five and one-half inches.

*Form.*—When first open: High centered. Permanence: Flattens, outer petals curl back.

*Petalage.*—Number of petals under normal conditions: 30–35.

*Color.*—The upper sides of the petals are Red Group 43A. The reverse sides of the petals are Red Group 53B. The base of each petal has a small (3/16"×3/16"), Green-White Group 157C, half moon at the point of attachment. The major color on the upper sides is Red Group 43A.

*Variegations.*—Occasional greenish-white streak on the guard petals.

*Discoloration.*—Color remains stable to petal drop at day 14 or 15.

*Fragrance.*—None.

Petals:

*Texture.*—Thick, leathery.

*Shape.*—Round to deltoid.

*Form.*—Tips slightly recurved.

*Arrangement.*—Imbricated. Petaloids in the center vary from none to sometimes 8, and have the same coloration as the petals. Petaloids are from ⅛" to ¼" in length, and 1/16" to ⅛" in width.

*Persistence.*—Petals drop off cleanly before drying.

*Lastingness.*—On the plant: Long (14–15 days). As a cut flower: Very long (18 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Light pink.

*Stigmas.*—Color: Greenish-White.

Plant:

*Form.*—Bush.

*Growth.*—Vigorous; upright; branching; compact. At maturity, height is twenty-four inches, width is eighteen inches in a garden setting in Somis, Calif. When grown as a pot rose in a 4"×3½" pot, the plant is seven to eight inches in height and five to six inches wide.

Foliage: Number of leaflets on normal mid-stem leaves: 5.

*Size.*—Small (3½" long×2½" wide).

*Quantity.*—Abundant.

*Color.*—New foliage: Upper and lower surfaces: Greyed-Orange Group 176B, but quickly turns green color of the mature leaf. Old foliage: Upper surface: Green Group 137B. Lower surface: Green Group 139C.

*Shape.*—Pointed oval.

*Texture.*—Upper side: Smooth.

*Edge.*—Serrated.

*Serration.*—Single, small.

*Petiole rachis.*—Color: Lower surface: Yellow-Green Group 147C. Upper surface: Greyed Purple Group 183C.

*Petiole underside.*—Smooth with occasional prickles.

*Stipules.*—Short (¼"), serrated, bearded.

*Disease resistance.*—Resistant to mildew under normal growing conditions at Sparrieshoop, Germany and Somis, Calif.

Wood:

*New wood.*—Color: Green Group 137D. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Short, straight.

*Color when young.*—Greyed-Purple Group 183C.

*Color when mature.*—Greyed-Orange Group 177C.

Small prickles:

*Quantity.*—On main stalks: None. On laterals: None.

I claim:

1. A new and distinct variety of miniature rose plant as herein shown and described characterized particularly by a compact, vigorous, upright habit of growth; ability to root quickly from softwood cuttings; rapid flowering; good shelf life as a pot rose; resistance to powdery mildew; and excellent flower color stability.

* * * * *

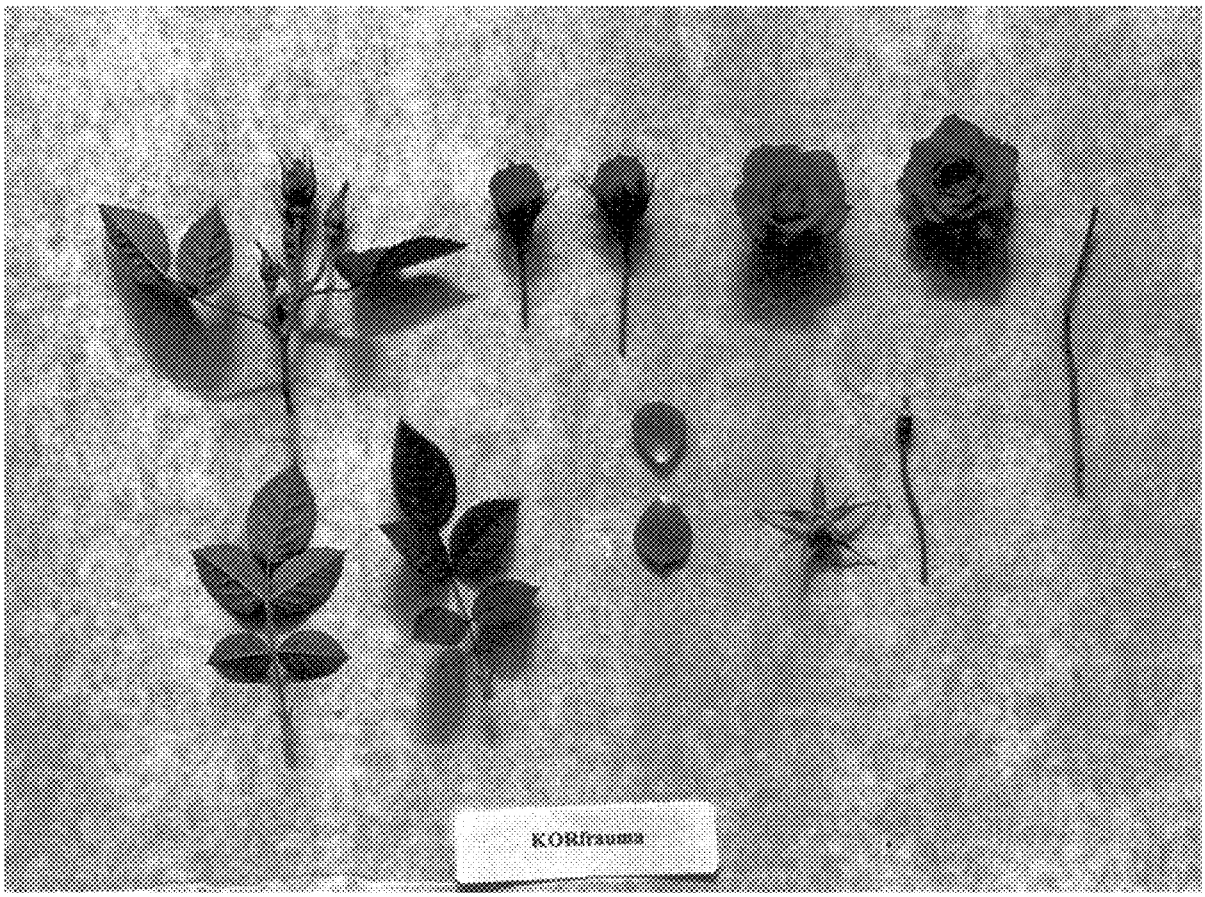
KORtrauma